(12) United States Patent
Bourdauducq

(10) Patent No.: US 6,407,219 B1
(45) Date of Patent: Jun. 18, 2002

(54) PROCESS FOR PREPARING AZOIMINOETHERS AND AZOCARBOXYLIC ACID ESTERS AND NOVEL AZOCBOXYLIC ACID MIXED ESTERS

(75) Inventor: Paul Bourdauducq, Chaponost (FR)

(73) Assignee: Atofina (FR)

( * ) Notice: Subject to any disclaimer, the term of this patent is extended or adjusted under 35 U.S.C. 154(b) by 0 days.

(21) Appl. No.: 09/889,147

(22) PCT Filed: Jan. 7, 2000

(86) PCT No.: PCT/FR00/00022

§ 371 (c)(1),
(2), (4) Date: Sep. 28, 2001

(87) PCT Pub. No.: WO00/42000

PCT Pub. Date: Jul. 20, 2000

(30) Foreign Application Priority Data

Jan. 15, 1999 (FR) .............................................. 99 00391

(51) Int. Cl.[7] ...................... C07C 257/06; C07C 245/04
(52) U.S. Cl. ...................... 534/588; 534/599; 534/738; 534/838; 534/886
(58) Field of Search ................................. 534/588, 599, 534/738, 838, 886

(56) References Cited

U.S. PATENT DOCUMENTS 4,950,742 A * 8/1990 Ichiriki et al. ............... 534/738

FOREIGN PATENT DOCUMENTS

EP 0 080 275 6/1983
EP 0 230 586 8/1987

OTHER PUBLICATIONS

Chemical Abstracts, vol. 109, No. 7, Aug. 15, 1988, Columbus, Ohio, U.S.; abstract No. 54300, Kelly, David P. et al.: "The cross–reaction between 1–(methoxycarbonyl)–and 1–(butoxycarbonyl)–1–methylethyl: sumultaneous generation of unlike radicals from an unsymmetrical azo precursor".

* cited by examiner

*Primary Examiner*—Fiona T. Powers
(74) *Attorney, Agent, or Firm*—Blank Rome LLP

(57) ABSTRACT

The invention concerns a method for preparing an azoiminoether hydrochloride which consists in reacting an azonitrile with an alcohol and hydrochloric acid in an aromatic solvent, wherein the molar ratio R=HCl/azonitrile is >2 when the alcohol is methanol and >3 when the alcohol is ethanol or a higher alcohol. The invention also concerns a method for preparing an azocarboxylic acid ester which consists in the synthesis of an azoiminoether hydrochloride by the inventive method and, hydrolysis in the presence of the resulting azoiminoether hydrochloride. Said methods enable to obtain liquid composition of azocarboxylic acid esters. The invention further concerns mixed azoiminoether salts of formula (II'). The invention also concerns mixed azoiminocarboxylic acid esters corresponding to the formula (III').

33 Claims, No Drawings

PROCESS FOR PREPARING AZOIMINOETHERS AND AZOCARBOXYLIC ACID ESTERS AND NOVEL AZOCBOXYLIC ACID MIXED ESTERS

A subject matter of the present invention is a process for the preparation of azoiminoethers (in the hydrochloride form) and their hydrolysis to azocarboxylic acid esters, these esters thus prepared being of use as free radical initiator in polymerization reactions. Another subject matter of the present invention is the mixed azoiminoethers thus prepared and the mixed esters of azocarboxylic acids deriving therefrom.

The preparation of azocarboxylic acid esters is conventionally carried out by a two-stage process comprising a first stage of conversion of the azonitrile by reaction with an alcohol in the presence of HCl according to the Pinner reaction, resulting in the corresponding azoiminoether hydrochloride, and a second stage of hydrolysis in the presence of water of the hydrochloride thus obtained.

This process exhibits a number of disadvantages which render it entirely unsuitable for production on an industrial scale. This is because it is too expensive, it is difficult to control, the purification of the final product is difficult and it requires a large excess of alcohol. Furthermore, it results in an inadequate yield and in a final product of unsatisfactory purity. Such a process is described, for example, by G. A. Mortimer in the Journal de chimie organique, page 1632-33 (1965), for the preparation of dimethyl azobisisobutyrate, used as intermediate in the synthesis of a polymerization initiator: azobisisobutyl diacetate.

Several solutions have been provided for solving some of these problems and thus allowing industrial scale production of the process for the preparation of azocarboxylic acid esters.

A process as described above, resulting in an increase in the yield and simultaneously in a significant reduction in the duration of the reaction and in a much better and much faster separation of the phases between the azodiisobutyric ester and the aqueous phase, is disclosed in DE 2 254 572. According to this patent, such improvements can be obtained by carrying out the Pinner conversion in the presence of a water-soluble cyclic ether and/or of a water-soluble diol of low MW and/or of an etherdiol or of a polyetherdiol, which is linear, of low MW ranging up to 1 800, in an amount of 0.001 to 11.0% by weight with respect to the aliphatic $C_1$–$C_6$ alcohol.

EP 80 275 dicloses that 2,2'-azobis(2-methylpropionitrile) and the related compounds can be converted using the Pinner reaction with an excellent yield with only the stoichiometric amount of the alcohol if the reaction is carried out in the presence of a compound comprising an ether group. It is disclosed that a faster conversion (and not a higher yield and/or a higher selectivity) can be obtained by increasing the concentration of HCl in the reaction mixture. However, the presence of ether presents problems, in particular with regard to the subsequent separation and treatment.

EP 230 586 has demonstrated that the preparation of azoiminoethers can be carried out in a single stage in a single receptacle according to a very easily controllable reaction, during which halogenation/oxidation of the hydrazonitrile and iminoetherification of the azonitrile take place. The preparation process according to EP 230 586 thus comprises the reaction of a hydrazonitrile with chlorine in the presence of an alcohol capable of converting the cyano group to an iminoether group in the presence of HCl (which is formed in situ). This reaction is carried out in a nonaqueous system in the presence of a solvent used in the halogenation/oxidation and iminoetherification, such as aromatic hydrocarbons, halogenated hydrocarbons and some other solvents. The amount of alcohol used varies between the theoretical amount required and 1.2 times this amount and the amount of chlorine varies between the theoretical amount and a slight excess. The final reaction product, corresponding to the azoiminoether hydrochloride, can be converted to an azoester by hydrolysis.

However, none of the above documents provides a process which can be used on an industrial scale, with a high yield and with a satisfactory purity, which makes it possible to dispense with awkward separation techniques.

The applicant company has demonstrated, surprisingly, a novel process for the preparation of azoiminoether salts and of the corresponding azocarboxylic acid esters which achieves the above aims. The present invention thus relates to a process for the preparation of azoiminoether salts by conversion of the azonitrile according to the Pinner reaction, in which invention the reaction is carried out in an aromatic solvent and in the presence of a large excess of HCl.

A subject matter of the present invention is thus a process for the preparation of an azoiminoether hydrochloride comprising the reaction of an azonitrile with an alcohol and hydrochloric acid in an aromatic solvent, in which process the molar ratio R=HCl/azonitrile is >2 when the alcohol is methanol and >3 when the alcohol is ethanol or a higher alcohol.

According to a specific embodiment, the azonitrile is formed in situ by reaction of the corresponding hydrazonitrile with chlorine.

According to another embodiment, the solvent is selected from the group consisting of toluene, chlorobenzene, xylene and benzene; chlorobenzene preferably being used when the azonitrile is formed in situ.

According to another embodiment, the alcohol is ethanol.

According to one embodiment, the alcohol used is composed of a mixture of alcohols, in particular a mixture comprising methanol, or methanol and ethanol.

According to one embodiment of the preparation process according to the invention, the azoiminoether hydrochloride corresponds to the formula (II)

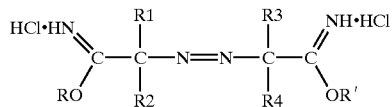

in which:

R1, R2, R3 and R4, which are identical or different, are independently selected from the group consisting of: linear or branched $C_1$–$C_9$ (preferably $C_1$–$C_4$) alkyls which are unsubstituted or substituted by one or more substituents selected from hydroxyl, $C_1$–$C_6$ alkoxy or halogen substituents;

$C_3$–$C_6$ cycloalkyls which are unsubstituted or substituted by one or more substituents selected from $C_1$–$C_6$ alkyl, $C_1$–$C_6$ alkoxy, hydroxyl or halogen;

$C_7$–$C_{12}$ aralkyls which are unsubstituted or substituted by one or more substituents selected from $C_1$–$C_6$ alkyl, $C_1$–$C_6$ alkoxy, hydroxyl or halogen;

$C_7$–$C_{12}$ aryls which are unsubstituted or substituted by one or more substituents selected from $C_1$–$C_6$ alkyl, $C_1$–$C_6$ alkoxy, hydroxyl or halogen;

it being possible for at least one of the R1–R2 and R3–R4 combinations optionally to form an aliphatic ring, R and R', which are identical or different, are independently selected from the group consisting of linear or branched $C_1$–$C_{10}$, preferably $C_1$–$C_4$, aliphatic radicals.

According to another embodiment of the present invention, in the formula (II), R and R' are different from one another and are selected from linear $C_1$–$C_4$ aliphatic radicals.

According to a specific embodiment, R1, R2, R3 and R4 are $C_1$–$C_4$ alkyl groups.

Another subject matter of the invention is a process for the preparation of an azocarboxylic acid ester comprising the synthesis of an azoiminoether hydrochloride by the process as defined above and the hydrolysis in the presence of water of the azoiminoether hydrochloride thus obtained.

According to one embodiment, the hydrolysis is carried out by successive addition of water to the reaction mixture or by running the reaction mixture into water, at a temperature of between 15° C. and 50° C., preferably approximately 30° C.

According to a specific embodiment of the process for the preparation of an azocarboxylic acid ester, after the synthesis stage, the azoiminoether hydrochloride is filtered off and washed with an organic solvent, and then the hydrolysis is carried out by gradual addition of the filtration cake to water at a temperature of between 15° C. and 50° C., preferably between 25° C. and 35° C.

An additional subject matter of the invention is a process for the preparation of a liquid composition of azocarboxylic acid esters comprising the synthesis of the azoiminoether hydrochloride by the process as described above, the hydrolysis of the salts thus obtained in the presence of water and the isolation of the organic phase comprising the esters.

According to a specific embodiment of this preparation process, the heaviest alcohol is reacted in a first step and then the lightest alcohol is reacted in a second step.

The invention also covers a liquid composition of azocarboxylic esters capable of being obtained by the process described above and in particular a composition which is liquid at a temperature of between –20° C. and 20° C.

According to one embodiment, the liquid composition comprises a first symmetrical ester of a first alcohol, a second symmetrical ester of a second alcohol and a mixed ester of these first and second alcohols. According to this embodiment, said first symmetrical ester is the methyl symmetrical ester, said second symmetrical ester is the ethyl symmetrical ester and said mixed ester is the methyl/ethyl ester.

Another subject matter of the invention is a process for the preparation of polymerization initiators comprising the synthesis of an azocarboxylic acid ester by the process for the preparation of azocarboxylic acid esters as described above and, if appropriate, the conversion of this ester to an initiator by known processes.

According to another aspect of the invention, a subject matter of the present invention is the mixed azoiminoether salts corresponding to the formula (II')

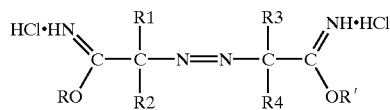

in which:

R1, R2, R3 and R4, which are identical or different, are independently selected from the group consisting of: linear or branched $C_1$–$C_9$ (preferably $C_1$–$C_4$) alkyls which are unsubstituted or substituted by one or more substituents selected from hydroxyl, $C_1$–$C_6$ alkoxy or halogen substituents;

$C_3$–$C_6$ cycloalkyls which are unsubstituted or substituted by one or more substituents selected from $C_1$–$C_6$ alkyl, $C_1$–$C_6$ alkoxy, hydroxyl or halogen;

$C_7$–$C_{12}$ aralkyls which are unsubstituted or substituted by one or more substituents selected from $C_1$–$C_6$ alkyl, $C_1$–$C_6$ alkoxy, hydroxyl or halogen;

$C_7$–$C_{12}$ aryls which are unsubstituted or substituted by one or more substituents selected from $C_1$–$C_6$ alkyl, $C_1$–$C_6$ alkoxy, hydroxyl or halogen;

it being possible for at least one of the R1–R2 and R3–R4 combinations optionally to form an aliphatic ring, R and R' are different from one another and are independently selected from the group consisting of linear or branched $C_1$–$C_{10}$, preferably $C_1$–$C_4$, aliphatic radicals. The invention preferably relates to azoiminoether salts in which R represents methyl and R' represents ethyl and in which R1, R2, R3 and R4 preferably represent $C_1$–$C_4$ alkyl groups.

Another subject matter of the present invention is the azocarboxylic acid esters obtained from the mixed azoiminoether salts as defined above.

Another subject matter of the present invention is a process for the preparation of an azoguanyl derivative comprising the synthesis of the corresponding azoiminoether hydrochloride by the process as described above and the reaction of the latter with ammonia or an amine in the presence of an alcohol by any known process appropriate for this purpose.

The invention is now described in more detail in the description which follows.

In the process for the preparation of the azoiminoether hydrochloride according to the invention, the starting azonitrile used in the Pinner conversion reaction can be symmetrical or asymmetrical. Mention may be made, as an example of such azonitriles, of azonitriles corresponding to the formula (I)

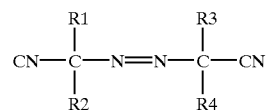

in which:

R1, R2, R3 and R4, which are identical or different, are independently selected from the group consisting of: linear or branched $C_1$–$C_9$ (preferably $C_1$–$C_4$) alkyls which are unsubstituted or substituted by one or more substituents selected from hydroxyl, $C_1$–$C_6$ alkoxy or halogen substituents;

$C_3$–$C_6$ cycloalkyls which are unsubstituted or substituted by one or more substituents selected from $C_1$–$C_6$ alkyl, $C_1$–$C_6$ alkoxy, hydroxyl or halogen;

$C_7$–$C_{12}$ aralkyls which are unsubstituted or substituted by one or more substituents selected from $C_1$–$C_6$ alkyl, $C_1$–$C_6$ alkoxy, hydroxyl or halogen;

$C_7$–$C_{12}$ aryls which are unsubstituted or substituted by one or more substituents selected from $C_1$–$C_6$ alkyl, $C_1$–$C_6$ alkoxy, hydroxyl or halogen;

it being possible for at least one of the R1–R2 and R3–R4 combinations optionally to form an aliphatic ring.

Concrete examples of such azonitriles are: 2,2'-azobisisobutyronitrile, 2,2'-azobis(2-methylbutyro-nitrile), 2,2'-azobis(2,4-dimethylvaleronitrile) and 1,1'-azobis(1-cyanocyclohexane).

As regards the alcohol used in the Pinner conversion reaction, use is made of linear or branched $C_1$–$C_{10}$ aliphatic alcohols, preferably linear and preferably $C_1$–$C_4$ alcohols. Ethanol and/or methanol is particularly preferred. The alcohol is used in an amount equal to the stoichiometric amount required or in a slight excess with respect to the latter, that is to say up to 1.5 times the theoretical value. The term "alcohol" is also understood to mean, in the context of the present invention, mixtures of the alcohols as defined above, preferably mixtures comprising at least methanol. In such a scenario, mixtures of esters are obtained. For example, if a methanol/ethanol mixture is used as reactant, a methyl ester, an ethyl ester and a mixed ethyl/methyl ester are obtained. The mixtures of alcohols also include mixtures of more than 2 alcohols, such as, for example, a methanol/ethanol/propanol mixture.

The hydrochloric acid is used in a large excess with respect to the stoichiometric amount required. The applicant company has demonstrated, surprisingly, first, that the HCl excess has to be very high (up to, for example, 3 times the stoichiometry) and, secondly, that the amount of HCl which has to be added also depends on the nature of alcohol used in the Pinner conversion stage. The HCl/azonitrile molar ratio R is >2 when it relates to methanol and this ratio is >3 when it relates to ethanol or a higher alcohol. In the case where mixtures of alcohols are used, the value of R is the weighted mean of the R values for each alcohol individually. For example, in the case of a molar 50/50 methanol/ethanol mixture, the R value of the HCl/azonitrile ratio of the mixture then generally fulfils the condition $R \geq 2+3/2=2.5$. R is between 2 and 6 for methanol and between 3 and 6, generally between 4 and 6, for the higher alcohols.

As regards the aromatic solvent, use may be made of any halogenated or nonhalogenated aromatic solvent which is sufficiently volatile to be removed at the end of the reaction by evaporation at a relatively low temperature under reduced pressure. Particularly appropriate solvents include chlorobenzene, toluene, xylene and benzene.

The Pinner conversion reaction is carried out at a temperature generally from 10 to 40° C., preferably from 15 to 25° C., for a period of time which varies according to the nature of the azonitrile and the reaction temperature and which is of the order of 8 to 24 h. The conversion reaction according to the invention is generally carried out in the following way: the solvent and the alcohol are mixed and azonitrile is added to the mixture thus obtained. The required amount of anhydrous hydrochloric acid is subsequently introduced into the reaction mixture in a known way while maintaining the temperature between 10 and 40° C., preferably between 15 and 25° C. The process can be carried out just as easily without pressure as under pressure.

According to a specific embodiment, the azonitrile is prepared in situ from the corresponding hydrazonitrile by reaction with chlorine and an alcohol capable of converting the cyano group to an iminoether group in the presence of HCl, as is disclosed in EP 230 586. However, in contrast to what is indicated in this document, the reaction has to be carried out in the presence of a large excess of HCl, as is defined above in connection with the Pinner conversion. In this scenario, the R ratio represents (HCl formed in situ+HCl added)/hydrazonitrile.

The reaction of the invention can be carried out for the dry hydrazonitrile but the applicant company has demonstrated that it is possible to carry it out starting from the wet hydrazonitrile. In this case, the water is removed by dissolution of the wet hydrazonitrile in the reaction solvent and separation of the aqueous phase by settling. The traces of water dissolved in the solvent can be removed by azeotropic entrainment before adding the alcohol and the other reactants.

The applicant company has also demonstrated, furthermore, that the in situ reaction, when it is carried out in the presence of a halogenated solvent, particularly a chlorinated solvent, preferably chlorobenzene, does not result in toxic chlorinated derivatives during the preparation of the azoiminoether salts.

The azoiminoether hydrochlorides thus prepared generally correspond to the formula (II)

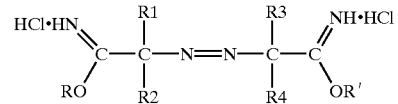

in which:
R1, R2, R3 and R4 is as defined above and
R and R', which are identical or different, are independently selected from the group consisting of linear or branched $C_1$–$C_{10}$, preferably $C_1$–$C_4$, aliphatic radicals; R and R' preferably being different.

The azoiminoether salts in which R1, R2, R3 and R4 and R and R' represent $C_1$ to $C_4$ alkyls are more particularly preferred.

The azoiminoether hydrochloride thus obtained can be used for the preparation of compounds of the azoguanyl type by reaction with gaseous ammonia or a primary or secondary amine in the presence of an alcohol by any known process appropriate for this purpose.

The azoiminoether hydrochloride thus obtained can also be used for the preparation of an azocarboxylic acid ester of formula (III)

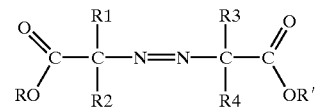

in which:
R1, R2, R3, R4, R and R' are as defined above in connection with the azoiminoether salts.

Another subject matter of the invention is the azocarboxylic acid esters of formula (III')

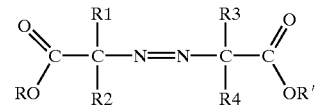

in which:
R1, R2, R3, R4, R and R' are as defined above in connection with the mixed azoiminoether salts (namely R and R' are different from one another).

For the preparation of the esters, at the end of the conversion of the azonitrile (reaction end which can be determined in a known way by infrared analysis of the CN band), a hydrolysis is carried out, optionally after isolation of the azoiminoether salt by filtration. At the end of the reaction, two clear phases are obtained. Separation by settling is allowed to take place until the phases have completely separated. The aqueous phase is removed and the remaining organic phase, comprising the azocarboxylic acid ester, is concentrated under reduced pressure to remove the solvent. An alternative form of the isolation of the final product consists, after the hydrolysis, in removing the reaction solvent by azeotropic entrainment with water under reduced pressure and in then separating the upper organic phase by settling.

To obtain a final product with a satisfactory purity, it is important to minimize the amount of azonitrile remaining in the final product, the decomposition products of azonitriles (in particular in the case of 2,2'-azobisisobutyronitrile, with the formation of tetramethylsuccinonitrile) being fairly toxic. In the case of the isolation of the azoiminoether hydrochloride by filtration and washing with an organic solvent (such as cyclohexane or toluene), purification is achieved, the azonitrile being soluble in these solvents. The hydrolysis can subsequently be carried out by gradual addition of the filtration cake to water at a temperature of 15 to 50° C., preferably between 25° C. and 35° C.

On the other hand, with the aim of avoiding the stage of filtration of a product of low stability, the applicant company has developed the hydrolysis by gradual addition of water to the suspension of azoiminoether hydrochloride in the reaction solvent or by running this suspension into water while controlling the temperature, for example at a value of between 15 and 50° C., preferably between 25 and 35° C.

The present invention also relates to a process for the preparation of a liquid composition of azocarboxylic acid (mixed and/or symmetrical) esters. This process comprises a first stage of synthesis of azoiminoether salts, either by reaction of azonitrile or by in situ synthesis of azonitrile from the corresponding hydrazonitrile in the presence of a mixture of alcohols as described above, then the hydrolysis of the salts obtained and the separation of the organic phase comprising the esters by any appropriate conventional technique. The liquid compositions thus obtained exhibit the advantage of being liquid at temperatures close to ambient temperature and, in some cases, down to −20° C., are easy to handle, do not give off dust, are nontoxic and do not comprise cyano groups. For the synthesis of these compositions, the various routes described in connection with the process for the preparation of the azocarboxylic acid esters are applicable (addition of water to the azoiminoether hydrochloride suspension, running this suspension into water, or filtration of the azoiminoether hydrochloride and addition of the filtration cake to water). Instead of starting from azonitrile, it is possible to start from the hydrazonitrile; in this case, chlorobenzene will preferably be used as reaction solvent. One way of promoting the formation of the mixed ester is to react the heaviest alcohol in a first step and then the lightest alcohol in a second step. The applicant company has also demonstrated that this synthesis of the mixed esters is also dependent on the excess of HCl added for the same mixture of starting alcohols.

Another subject matter of the present invention is a process for the preparation of polymerization initiators comprising the synthesis of an azocarboxylic acid ester by the process as described above and, if appropriate, the conversion of this ester into an initiator by known processes. The invention also applies to the preparation of all the compounds which can derive from the azocarboxylic acid esters, such as: the corresponding alcohols and acetates and the corresponding alkanes, acids and amides.

The mixed azoiminoether salts which are more particularly preferred are those derived from a mixture of alcohols selected from: methanol, ethanol, n-propanol and n-butanol, preferably from a mixture comprising at least methanol.

The azocarboxylic acid esters obtained from these mixed ethers also form part of the present invention.

The following examples are given purely by way of illustration and without implied limitation of the invention.

EXAMPLES

Example 1

164 g (1 mol) of 2,2'-azobisisobutyronitrile are added to a mixture comprising 600 g of toluene and 76.8 g of methanol or 110.4 g of ethanol (2.4 mol). Gaseous hydrochloric acid is added over 4–5 hours while cooling at 15–20° C. The mixture is kept stirred at approximately 20° C. for 16 hours.

The mixture is filtered and then the filtration cake is washed with 2 times 100 g of cyclohexane. The azoiminoether hydrochloride cake is slowly added to 600 g of water at a temperature of approximately 30° C. After stirring for 1 hour at approximately 30° C., the reaction mixture is cooled to approximately 10° C. The aqueous and organic phases are separated by separating the organic phase by settling and extracting the aqueous phase with 100 g of cyclohexane. The organic phases thus obtained are combined and concentrated under reduced pressure at approximately 35° C.

This process is employed for various values of the HCl/azonitrile molar ratio as indicated in Table 1 below. The azoester yield obtained and the nature of the alcohol are shown in Table 1.

TABLE 1

| Alcohol | R ratio: HCl/azonitrile | Azoester yield (%) |
| --- | --- | --- |
| $CH_3OH$ | 2.0 | 86 |
|  | 2.6 | 90.5 |
|  | 3.0 | 91.0 |
| $C_2H_5OH$ | 2.0 | 25.0 |
|  | 2.6 | 52.0 |
|  | 3.2 | 60.0 |
|  | 4.0 | 84.0 |
|  | 4.4 | 91.0 |
|  | 4.8 | 91.0 |

These results clearly demonstrate that the HCl/azonitrile ratio has a strong influence on the reaction yield and that the yield depends on the nature of the alcohol.

This result was also confirmed by carrying out the examples of the synthesis of azoiminoether which are disclosed in EP 230 586 while varying the nature of the alcohol in Example 2 below.

Example 2

166 g of 2,2'-hydrazobisisobutyronitrile (1 mol) are added to a mixture of 640 g of toluene and 76.8 g of methanol or 110.4 g of ethanol (2.4 mol). 74.6 g of chlorine (1.05 mol, which results, by reaction with 1 mol of hydrazonitrile, in the in situ formation of 2.0 mol of HCl) are added while cooling at 15–20° C. The mixture is stirred for 5 hours at 25° C. and then for 15 hours at approximately 20° C. The subsequent stages are carried out under operating conditions identical to those described in the preceding example. The HCl/azonitrile ratio is in this instance approximately 2.6, corresponding to the sum of 2.0 mol formed in situ and 0.6 mol added.

With methanol, the azoester yield is 88% whereas, with ethanol, the yield is only 25%.

The same tests, carried out starting from the hydrazo compound while adding hydrochloric acid (0.6 mol in the case of methanol and 2.4 mol in the case of ethanol, which results in R ratios of approximately 2.6 and 4.4 respectively) after chlorination, made it possible to obtain azoester yields of 91 and 90% respectively. In this case, after addition of the chlorine, 21.9 g of hydrochloric acid (0.6 mol) are added over approximately 1 hour at a temperature of 15–20° C. in the test with methanol and 87.6 g of hydrochloric acid (2.4 mol) are added over approximately 2 hours at a temperature of 15–20° C. in the test with ethanol. The mixtures are subsequently kept stirred for 15 hours at 20° C., the subsequent stages being identical to those described above.

Example 3

200 g of wet 2,2'-hydrazobisisobutyronitrile (1 mol) are added to 600 g of toluene while heating at approximately 35° C. to obtain dissolution of the hydrazobisisobutyronitrile. The lower aqueous phase, i.e. 31 g, is separated by settling. The water dissolved in toluene is removed by azeotropic entrainment under vacuum. 110.4 g of ethanol (2.4 mol) and 0.2 g of sodium bromide, used as chlorination catalyst, are added. 74.6 g of chlorine (1.05 mol, which results in the in situ formation of 2.0 mol of HCl) are added over 2 hours while cooling at approximately 20° C., followed, over 3 hours, by 87.6 g of hydrochloric acid (2.4 mol). The R ratio is approximately 4.4. The reaction mixture is kept stirred overnight at 20° C. The mixture thus obtained is subsequently run into 600 g of water preheated to approximately 25° C. without exceeding 30° C. The mixture is stirred for 1 hour at 30° C. The toluene is removed by azeotropic entrainment under vacuum at a temperature of 35° C. The upper organic phase is separated by settling. The azoester yield is 91% and the azonitrile content in the final product is 0.3%.

Tests carried out under the same conditions but replacing the ethanol with methanol gave, with addition of 0.6 mol of hydrochloric acid (instead of 2.4), 0.8% of azonitrile in the final product. Without addition of HCl, 5% of azonitrile remains in the final product.

Example 4

200 g of wet 2,2'-hydrazobisisobutyronitrile (1 mol) are added to 750 g of chlorobenzene while heating at approximately 30° C. to obtain dissolution of the hydrazobisisobutyronitrile. The upper aqueous phase, i.e. 30 g, is separated by settling. The water dissolved in the chlorobenzene is removed by azeotropic entrainment under vacuum. 76.8 g of methanol (2.4 mol) and 0.2 g of sodium bromide are added. 74.6 g of chlorine (1.05 mol, which results in the in situ formation of 2.0 mol of HCl) are added while cooling at approximately 15° C., followed by 21.9 g of hydrochloric acid (0.6 mol). The reaction mixture is stirred for 18 hours at approximately 20° C. The mixture is subsequently run into 600 g of water over approximately 1 hour; the temperature is allowed to reach approximately 30° C. and then cooling is applied in order for the temperature not to exceed this value. The mixture is subsequently stirred at approximately 30° C. for 1 hour in order to obtain clear aqueous and organic phases. The chlorobenzene is removed by azeotropic entrainment under vacuum at a temperature of 35° C. The upper organic phase is separated by settling. The azoester yield thus obtained is 92%.

Example 5

164 g of 2,2'-azobisisobutyronitrile (1 mol) are added to a mixture of 600 g of toluene, 51.2 g of methanol (1.6 mol) and 36.8 g of ethanol (0.8 mol). Gaseous hydrochloric acid is added over 4–5 hours while cooling at 15–20° C. The reaction mixture is kept stirred for 16 hours at 20° C. The mixture is run into 600 g of water over 1 hour while allowing the temperature to rise to approximately 30° C. The resulting mixture is stirred for 1 hour at 30° C. in order to obtain clear aqueous and organic phases. The toluene is removed by azeotropic entrainment under vacuum at a temperature of approximately 35° C. and then the upper organic phase is separated by settling.

Products are obtained, with yields in the region of 85%, which are clear at ambient temperature, which have different compositions according to the amount of hydrochloric acid used and which set solid at different temperatures with cooling.

TABLE 2

| | R (moles) HCl/azonitrile | | |
|---|---|---|---|
| Composition, molar % | 2.6 | 3.3 | 4.3 |
| A | nd | 60.0 | 61.0 |
| B | nd | 25.0 | 30.0 |
| C | nd | 4.0 | 6.0 |
| Various | nd | 11.0 | 3.0 |
| —COOCH$_3$/—COOC$_2$H$_5$ molar ratio | nd | 4.4 | 3.6 |
| Solidification temperature (° C.) | appr. 10 | appr. 5 | appr. 0 |
| Liquid homogeneous at (° C.) | appr. 20 | appr. 15 | appr. 10 |

A being the methyl ester of 2,2'-azobisiso-butyrique acid

B being the methyl/ethyl ester of 2,2'-azobisiso-butyric acid

C being the ethyl ester of 2,2'-azobisiso-butyrique acid nd meaning not determined.

The molar ratio is calculated by dividing the total number of —COOCH$_3$ groups by the total number of —COOC$_2$H$_5$ groups present in the final mixture.

By way of comparison, mixtures of the product A (solid with a melting point of 26 to 29° C.) and the product C (liquid down to –20° C.) which are prepared separately do not give liquids at ambient temperature under the same —COOCH$_3$/—COOC$_2$H$_5$ molar ratios but solid/liquid mixtures and rapidly set solid with cooling at 15° C.

By varying the ratio of the alcohols with respect to one another, the composition of the mixtures is varied. Thus, by operating as described above but with 4.3 mol of hydrochloric acid and with, as alcohol:

a) 1.2 mol of methanol=38.4 g+1.2 mol of ethanol=55.2 g;

b) 1.6 mol of methanol=51.2 g+0.8 mol of ethanol=36.8 g;

c) 2.0 mol of methanol=64 g+0.4 mol of ethanol=18.4 g, the following results are obtained, with A, B and C having the above meanings.

TABLE 3

| Composition, molar % | a | b | c |
|---|---|---|---|
| A | 40.0 | 61.0 | 81.0 |
| B | 38.0 | 30.0 | 15.0 |
| C | 18.5 | 6.0 | 1.0 |
| Various | 3.5 | 3.0 | 3.0 |
| Molar ratio | | | |
| —COOCH$_3$/—COOC$_2$H$_5$ | 1.5 | 3.6 | 10.5 |
| Solidification temperature (C.°) | appr. –10 | appr. 0 | appr. 15 |
| Liquid homogeneous at (° C.) | appr. 5 | appr. 10 | appr. 20 |

By way of comparison, a product prepared by mixing A and C in a molar ratio of 1.5 gives a solid/liquid mixture from approximately 15° C. and, in a molar ratio of 3.6, sets solid at approximately 15° C.

Example 6 a) 64.2 g of gaseous hydrochloric acid (1.76 mol) are added over 2 hours, while cooling at 15–20° C., to a mixture of 600 g of toluene, 164 g of 2,2'-azobisiso-butyronitrile and 36.8 g of ethanol (0.8 mol). The mixture is kept stirred for 4 hours at 20° C. 51.2 g of methanol (1.6 mol) are subsequently added and then, while cooling at 15–20° C., 92.7 g of gaseous hydrochloric acid (2.54 mol) are added over 2 hours 30'. The reaction mixture is kept stirred for 15 hours at approximately 15° C. The suspension obtained is run into 600 g of water preheated to approximately 25° C. without exceeding 30° C. The mixture is stirred at 30° C. for approximately 1 hour. The toluene is removed by azeotropic entrainment under vacuum at a temperature of approximately 35° C. The upper organic phase is separated by settling.

b) The following reaction is carried out under the same reaction conditions: the addition of 55.2 g of ethanol (1.2 mol) and 96.4 g of gaseous hydrochloric acid (2.64 mol) in a first step and then 38.4 g of methanol (1.2 mol) and 60.6 g of gaseous hydrochloric acid (1.66 mol) in a second step.

The physical characteristics of the compositions thus obtained are recorded in Table 4 below.

TABLE 4

| Example 6 | (a) | (b) |
|---|---|---|
| Solidification Temperature (° C.) | 0 | −20 |
| Liquid homogeneous at (° C.) | 5 | −5 |

By this addition of the heaviest alcohol first, the solidification temperature and the temperature for obtaining a homogeneous liquid are observed to fall (see the comparison with Example 5, a and b).

What is claimed is:

1. A process for the preparation of an azoiminoether hydrochloride comprising the reaction of an azonitrile with an alcohol and hydrochloric acid in an aromatic solvent, in which process the molar ratio R=HCl/azonitrile is >2 when the alcohol is methanol and >3 when the alcohol is ethanol or a higher alcohol.

2. The process as claimed in claim 1, in which the azonitrile is formed in situ by reaction of the corresponding hydrazonitrile with chlorine.

3. The process as claimed in claim 1, in which the solvent is selected from the group consisting of toluene, chlorobenzene, xylene and benzene.

4. The process as claimed in claim 1, in which the alcohol used is composed of a mixture of alcohols.

5. The process as claimed in claim 1, in which the alcohol is methanol and/or ethanol.

6. The preparation process as claimed in claim 1, in which the azoiminoether hydrochloride corresponds to the formula (II)

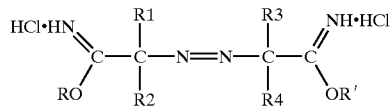

in which:
R1, R2, R3 and R4, which are identical or different, are independently selected from the group consisting of:
linear or branched $C_1$–$C_9$ alkyls which are unsubstituted or substituted by one or more substituents selected from hydroxyl, $C_1$–$C_6$ alkoxy or halogen substituents;
$C_3$–$C_6$ cycloalkyls which are unsubstituted or substituted by one or more substituents selected from $C_1$–$C_6$ alkyl, $C_1$–$C_6$ alkoxy, hydroxyl or halogen;
$C_7$–$C_{12}$ aralkyls which are unsubstituted or substituted by one or more substituents selected from $C_1$–$C_6$ alkyl, $C_1$–$C_6$ alkoxy, hydroxyl or halogen;

$C_7$–$C_{12}$ aryls which are unsubstituted or substituted by one or more substituents selected from $C_1$–$C_6$ alkyl, $C_1$–$C_6$ alkoxy, hydroxyl or halogen;
it being possible for at least one of the R1-R2 and R3-R4 combinations optionally to form an aliphatic ring,
R and R', which are identical or different, are independently selected from the group consisting of linear or branched $C_1$–$C_{10}$.

7. The preparation process as claimed in claim 6, in which, in the formula (II), R and R' are different from one another and are selected from linear $C_1$–$C_4$ aliphatic radicals.

8. The preparation process as claimed in claim 6, in which, in the formula (II), R1, R2, R3 and R4 are $C_1$–$C_4$ alkyl groups.

9. The preparation process as claimed in claim 6, in which the solvent is chlorobenzene and the alcohol is a mixture of methanol and ethanol.

10. The preparation process as claimed in claim 9, in which, in the formula (II), R and R' are different from one another and are selected from linear $C_1$–$C_4$ aliphatic radicals, and R1, R2, R3 and R4 are $C_1$–$C_4$ alkyl groups.

11. A process for the preparation of an azocarboxylic acid ester comprising the synthesis of an azoiminoether hydrochloride by the process defined in claim 1 and the hydrolysis in the presence of water of the azoiminoether hydrochloride thus obtained.

12. The preparation process as claimed in claim 11, in which the hydrolysis is carried out by successive addition of water to the reaction mixture or by running the reaction mixture into water, at a temperature of between 15° C. and 50° C.

13. The preparation process as claimed in claim 11, in which, after the synthesis, the azoiminoether hydrochloride is separated by filtration, washed with an organic solvent and hydrolyzed by gradual addition of the filtration cake to water at a temperature of between 15° C. and 50° C.

14. A process for the preparation of an azocarboxylic acid ester comprising the synthesis of an azoiminoether hydrochloride by the process defined in claim 10 and the hydrolysis in the presence of water of the azoiminoether hydrochloride thus obtained.

15. The preparation process as claimed in claim 14, in which the hydrolysis is carried out by successive addition of water to the reaction mixture or by running the reaction mixture into water, at a temperature of between 15° C. and 50° C.

16. The preparation process as claimed in claim 14, in which, after the synthesis, the azoiminoether hydrochloride is separated by filtration, washed with an organic solvent and hydrolyzed by gradual addition of the filtration cake to water at a temperature of between 15° C. and 50° C.

17. A process for the preparation of a liquid composition of azocarboxylic acid esters comprising the synthesis of azoiminoether hydrochloride as claimed in claim 4, the hydrolysis of the salts thus obtained in the presence of water and the isolation of the organic phase comprising the esters.

18. The preparation process as claimed in claim 17, in which the heaviest alcohol is reacted in a first step and then the lightest alcohol is reacted in a second step.

19. A liquid composition of azocarboxylic acid esters capable of being obtained by the process as claimed in claim 17.

20. The liquid composition of azocarboxylic acid esters as claimed in claim 19, which is liquid at a temperature of between −20° C. and 20° C.

21. The liquid composition of azocarboxylic acid esters as claimed in claim 19, comprising a first symmetrical ester of a first alcohol, a second symmetrical ester of a second alcohol and a mixed ester of these first and second alcohols.

22. The liquid composition of azocarboxylic acid esters as claimed in claim 21, in which said first symmetrical ester is the methyl symmetrical ester, said second symmetrical ester is the ethyl symmetrical ester and said mixed ester is the methyl/ethyl ester.

23. A process for the preparation of polymerization initiators comprising the synthesis of an azocarboxylic acid ester by the process as claimed in claim 11 and, optionally, the conversion of this ester to an initiator by known processes.

24. A mixed azoiminoether salt of formula (II')

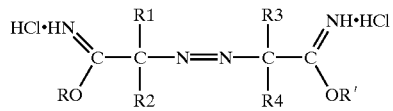

in which:
R1, R2, R3 and R4, which are identical or different, are independently selected from the group consisting of:
linear or branched $C_1$–$C_9$ alkyls which are unsubstituted or substituted by one or more substituents selected from hydroxyl, $C_1$–$C_6$ alkoxy or halogen substituents;
$C_3$–$C_6$ cycloalkyls which are unsubstituted or substituted by one or more substituents selected from $C_1$–$C_6$ alkyl, $C_1$–$C_6$ alkoxy, hydroxyl or halogen;
$C_7$–$C_{12}$ aralkyls which are unsubstituted or substituted by one or more substituents selected from $C_1$–$C_6$ alkyl, $C_1$–$C_6$ alkoxy, hydroxyl or halogen;
$C_7$–$C_{12}$ aryls which are unsubstituted or substituted by one or more substituents selected from $C_1$–$C_6$ alkyl, $C_1$–$C_6$ alkoxy, hydroxyl or halogen;
it being possible for at least one of the R1–R2 and R3–R4 combinations optionally to form an aliphatic ring,
R and R' are different from one another and are independently selected from the group consisting of linear or branched $C_1$–$C_{10}$.

25. The azoiminoether salt as claimed in claim 24, in which, in the formula (II'), R represents methyl and R' represents ethyl.

26. The azoiminoether salt as claimed in claim 24, in which, in the formula (II'), R1, R2, R3 and R4 represent $C_1$–$C_4$ alkyl groups.

27. The azoiminoether salt as claimed in claim 24, in which, in the formula (II'), R represents methyl, R' represents ethyl and R1, R2, R3 and R4 represent $C_1$–$C_4$ alkyl groups.

28. A mixed ester of azocarboxylic acid corresponding to the formula (III')

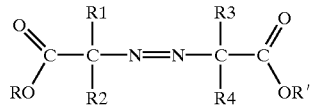

in which:
R1, R2, R3, R4, R and R' are as defined in claim 24, it being understood that the mixed ester of azocarboxylic acid is not methyl butyl isobutyrate.

29. A process for the preparation of an azoguanyl derivative comprising the preparation of an azoiminoether hydrochloride by the process as claimed in claim 1 and the reaction of the latter with ammonia or an amine in the presence of an alcohol.

30. An azoguanyl derivative capable of being obtained by the process as claimed in claim 29.

31. The preparation process as claimed in claim 12, wherein said temperature is between 25° C. and 35° C.

32. The preparation process as claimed in claim 13, wherein said temperature is between 25° C. and 35° C.

33. The preparation process as claimed in claim 16, wherein said temperature is between 25° C. and 35° C.

* * * * *